US011518736B2

(12) United States Patent
Burckhardt et al.

(10) Patent No.: US 11,518,736 B2
(45) Date of Patent: Dec. 6, 2022

(54) BLOCKING AGENT FOR AMINES, LATENT HARDENERS AND POLYURETHANE COMPOSITIONS

(71) Applicant: SIKA TECHNOLOGY AG, Baar (CH)

(72) Inventors: Urs Burckhardt, Zürich (CH); Andreas Kramer, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 402 days.

(21) Appl. No.: 16/618,820

(22) PCT Filed: Jun. 19, 2018

(86) PCT No.: PCT/EP2018/066179
§ 371 (c)(1),
(2) Date: Dec. 3, 2019

(87) PCT Pub. No.: WO2018/234268
PCT Pub. Date: Dec. 27, 2018

(65) Prior Publication Data

US 2021/0246101 A1 Aug. 12, 2021

(30) Foreign Application Priority Data

Jun. 19, 2017 (EP) .................................... 17176691

(51) Int. Cl.

| | |
|---|---|
| ***C07C 251/24*** | (2006.01) |
| ***C07C 249/02*** | (2006.01) |
| ***C08G 18/12*** | (2006.01) |
| ***C08G 18/32*** | (2006.01) |
| ***C08G 18/48*** | (2006.01) |
| ***C08G 18/75*** | (2006.01) |
| ***C08G 18/76*** | (2006.01) |
| ***C08L 75/08*** | (2006.01) |

(52) U.S. Cl.
CPC .......... *C07C 251/24* (2013.01); *C07C 249/02* (2013.01); *C08G 18/12* (2013.01); *C08G 18/3256* (2013.01); *C08G 18/4812* (2013.01); *C08G 18/4825* (2013.01); *C08G 18/4837* (2013.01); *C08G 18/755* (2013.01); *C08G 18/7671* (2013.01); *C08L 75/08* (2013.01)

(58) Field of Classification Search
CPC ..... C07C 251/24; C07C 249/02; C08G 18/12; C08G 18/3256; C08G 18/4812; C08G 18/4825; C08G 18/4837; C08G 18/755; C08G 18/7671; C08L 75/08
See application file for complete search history.

(56) References Cited

U.S. PATENT DOCUMENTS

| | | | | |
|---|---|---|---|---|
| 2006/0122352 | A1 | 6/2006 | Burckhardt | |
| 2008/0114146 | A1 | 5/2008 | Burckhardt | |
| 2010/0273924 | A1* | 10/2010 | Burckhardt ........ | C08G 18/4812 524/189 |
| 2015/0111991 | A1 | 4/2015 | Kitamura et al. | |

FOREIGN PATENT DOCUMENTS

| | | | |
|---|---|---|---|
| CN | 1678653 | A | 10/2005 |
| CN | 104350033 | A | 2/2015 |
| JP | S48-096559 | A | 12/1973 |
| JP | S51-004138 | A | 1/1976 |
| JP | WO2013/179915 | A1 | 1/2016 |
| WO | 2004/013200 | A1 | 2/2004 |

OTHER PUBLICATIONS

Jan. 2, 2020 English Translation of International Preliminary Report on Patentability issued in International Patent Application No. PCT/EP2018/066179.

Sep. 12, 2018 International Search Report issued in International Patent Application No. PCT/EP2018/066179.

* cited by examiner

*Primary Examiner* — Patrick D Niland
(74) *Attorney, Agent, or Firm* — Oliff PLC

(57) ABSTRACT

The use of an aldehyde mixture containing 70 to 95 wt % of aldehydes of formula (I) and 5 to 30 wt % of alkylbenzene compounds not corresponding to formula (I) as a blocking agent for amines results in odorless, especially economically blocked amines, which at room temperature are typically liquid and have a surprisingly low viscosity. Such blocked amines are particularly suitable as latent hardeners in isocyanate-group-containing compositions. Single-component moisture-curing polyurethane compositions formulated therewith are surprisingly stable in storage, can be used for low-emission applications without odor problems and do not trigger any problems with plasticizer migration. Surprisingly, said compositions even have advantages over corresponding compositions having latent hardeners based on purified aldehydes of formula (I), in particular with respect to viscosity, storage stability and especially strength.

15 Claims, No Drawings

BLOCKING AGENT FOR AMINES, LATENT HARDENERS AND POLYURETHANE COMPOSITIONS

TECHNICAL FIELD

The invention relates to a blocking agent for amines, to latent hardeners and to polyurethane compositions thereof, especially for application as elastic adhesives, sealants and coatings.

STATE OF THE ART

Polyurethane compositions which crosslink through reaction of isocyanate groups with moisture or water and cure to give elastomers are especially used as adhesives, sealants or coatings in the construction and manufacturing industry, for example for component bonding in assembly, for filling joints, as floor coating or as roof seal. Owing to their good adhesion and elasticity, they can gently damp forces acting on the substrates, triggered for instance by vibrations or variations in temperature. When compositions of this kind are used at high humidity and/or elevated temperature, however, the curing thereof often proceeds with disruptive blistering that impairs adhesion and strength as a result of carbon dioxide gas released, which is not dissolved or dissipated quickly enough. In order to avoid blistering, it is possible to add chemically blocked amines to the compositions, called latent hardeners, which bind moisture through hydrolysis and release amino groups which react with the isocyanate groups without forming carbon dioxide. Latent hardeners used are usually compounds having aldimine, ketimine or oxazolidine groups. However, the known latent hardeners are often accompanied by the disadvantage of being highly viscous oils or solids at room temperature and of accordingly placing increased demands on the handling thereof, for example by having to be melted or dissolved. Furthermore, they may have an unsatisfactory latency, so that they, on storage in compositions containing isocyanate groups, trigger premature crosslinking reactions of the isocyanate groups and hence lower the storage stability of the composition and/or accelerate the curing thereof to such a degree as to result in too short an open time and hence too small a working window. Moreover, many of the known latent hardeners, on curing, lead to troublesome immissions caused by highly volatile, intensely odorous, aldehydes or ketones which serve as blocking agents in the latent hardener and are released through hydrolysis.

WO 2004/013200 discloses polyurethane compositions comprising latent hardeners, the blocking agents of which are nonvolatile and accordingly remain in the cured composition. These compositions are completely odorless and can therefore also be used in interior spaces or in large-area applications, without causing immission problems. However, they have various disadvantages. The nonvolatile blocking agent acts as plasticizer in the cured composition, which can lower the mechanical strength or stiffness. The elevated content of plasticizer often leads to increased plasticizer migration, which can be manifested in bleeding, a tacky, slightly soiling surface of the composition, contamination of or damage to the substrates, or in problems with coverage, especially overcoating, overpainting, overlayering or overbonding, of the composition.

A nonvolatile instead of a volatile blocking agent eventually also results in clearly higher costs. On the one hand, owing to its higher mass, more blocking agent on a quantitative basis is required and, on the other hand, the purification thereof is expensive, since it, for example, has to be distilled under high vacuum at high temperatures, which requires expensive equipment, takes a long time and often produces low yields because of polymer formation and other decomposition reactions under the high temperatures required.

WO 2013/179915 describes branched long-chain alkylbenzaldehydes which, in distilled or fractionated form, are used as blocking agent in amine components of epoxy resin compositions. In the distillation or fractionation, as described in Example 2, the aldehydes are distilled overhead and collected as main fraction with a boiling point of 187 to 230° C. at 8 Torr and used further. In the course of this, highly volatile fractions and especially also the high-boiling-point byproducts were separated.

DESCRIPTION OF THE INVENTION

It is accordingly an object of the present invention to make available an economical blocking agent for amines, which makes possible the preparation of inexpensive blocked amines or latent hardeners, which are liquid and of low viscosity at room temperature, cause no immissions and problems with plasticizer migration and are storage-stable together with isocyanate groups. This object is achieved with the blocking agent, described in claim 1, in the form of an aldehyde mixture which contains, as main constituent, alkylbenzaldehydes and, as secondary constituents, additional mainly high-boiling-point alkylbenzene compounds. The aldehyde mixture can especially be obtained as unpurified or only slightly purified crude product of a formylation of alkylbenzenes and is extremely economical; it thereby also gives clearly more inexpensive blocked amines than if corresponding purified blocking agents are used, from which the high-boiling-point fractions have been removed. Surprisingly, the properties of the blocked amines themselves and of the compositions containing isocyanate groups which contain these blocked amines as latent hardeners are not harmed by the secondary constituent of the blocking agent according to the invention, but surprisingly even improved. The blocked amines according to the invention are, at room temperature, typically liquid and of low viscosity and can accordingly be used simply and without solvent. Surprisingly, they are even of lower viscosity than the latent hardeners prepared with corresponding purified blocking agents after removal of the high-boiling-point constituent, which is astonishing in view of the increased molecular weight and of the partial aldehyde functionality of the secondary constituent, with results in high-molecular-weight condensation products. Furthermore, they have a lower crystallization temperature and thereby remain liquid for a very long time on storage under cold conditions. Finally, they are, despite purification of the blocking agent being absent, surprisingly light-colored and have an astonishingly good latency with regard to isocyanates.

Moisture-curing polyurethane compositions formulated with the latent hardeners according to the invention are of low viscosity, storable for a long time, readily processable, without an odor problem, even in interior spaces, usable for large-area and for low-emission applications and have a long open time with fast curing. In the cured state, they have good mechanical properties with high elasticity and low tendency for plasticizer migration. Surprisingly, they show, in places, in comparison with analogous compositions with latent hardeners from corresponding purified blocking agents, even better properties with regard to the viscosity, storage stability and the mechanical characteristics, especially the strength.

Further aspects of the invention are the subject of further independent claims.

Particularly preferred embodiments of the invention are the subject of the dependent claims.

Ways of Executing the Invention

The invention provides for the use of an aldehyde mixture comprising

70% to 95% by weight of aldehydes of the formula (I), in which R is an alkyl radical having 6 to 20 carbon atoms, and (I)

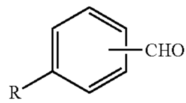

5% to 30% by weight of alkylbenzene compounds not corresponding to the formula (I), as blocking agent for amines.

The aldehyde mixture preferably contains 70% to 92% by weight of aldehydes of the formula (I) and 8% to 30% by weight of alkylbenzene compounds not corresponding to the formula (I).

Especially, the alkylbenzene compounds not corresponding to the formula (I) have a higher boiling point than the aldehydes of the formula (I).

Preferably, R are alkyl radicals having 8 to 16 carbon atoms, especially having 10 to 14 carbon atoms.

Particularly preferably, R are alkyl radicals having 10 to 14 carbon atoms and the alkylbenzene compounds not corresponding to the formula (I) have a molecular weight of at least 350 g/mol.

Preferably, the alkyl radicals R are predominantly branched.

Especially, R are predominantly branched alkyl radicals having 10 to 14 carbon atoms. Such aldehydes produce especially low-viscosity blocked amines.

Particularly preferably, R are radicals of the formula $$\text{----}\!\!\!<\begin{matrix}R^1\\R^2\end{matrix},$$

where $R^1$ and $R^2$ each time are alkyl radicals and together each time have 9 to 13 carbon atoms.

The formyl group is preferably in the meta or para position with respect to the radical R.

Particularly preferably, the formyl group is in the para position.

Very particularly preferably, the aldehydes of the formula (I) thus represent aldehydes of the formula (I a), in which $R^1$ and $R^2$ have the meanings already given.

(Ia)

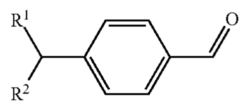

Particularly preferred aldehydes of the formula (I) are 4-decylbenzaldehyde, 4-undecylbenzaldehyde, 4-dodecylbenzaldehyde, 4-tridecylbenzaldehyde and 4-tetradecylbenzaldehyde, in which the 4-alkyl radicals are branched.

The aldehydes of the formula (I) are preferably selected from 4-decylbenzaldehydes, 4-undecylbenzaldehydes, 4-dodecylbenzaldehydes, 4-tridecylbenzaldehydes and 4-tetradecylbenzaldehydes, the alkyl radicals of which are predominantly branched.

The alkylbenzene compounds not corresponding to the formula (I) are mainly high molecular weight than the aldehydes of the formula (I) and partially aldehyde-functional.

They preferably comprise one or more compounds of the formulae

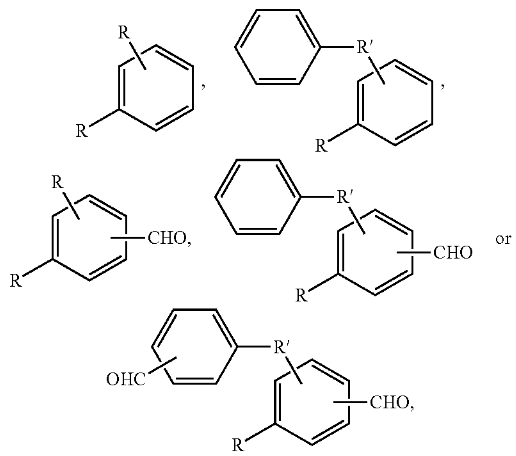

in which R' is an alkylene radical having 6 to 20 carbon atoms and R has the meanings already described.

Such high molecular weight compounds are separated on purification of a mixture of aldehydes of the formula (I) through overhead distillation or fractionation, since they have a substantially higher boiling point than the corresponding aldehydes of the formula (I), they being typically removed as waste as what is called bottoms. In the use according to the invention, they are, however, used together with the aldehydes of the formula (I), which surprisingly results in the unexpected advantages described.

Particularly preferably, the aldehyde mixture contains 5% to 30% by weight, especially 8% to 30% by weight, of alkylbenzene compounds selected from compounds of the formulae

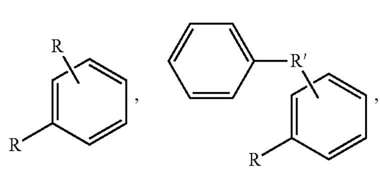

-continued

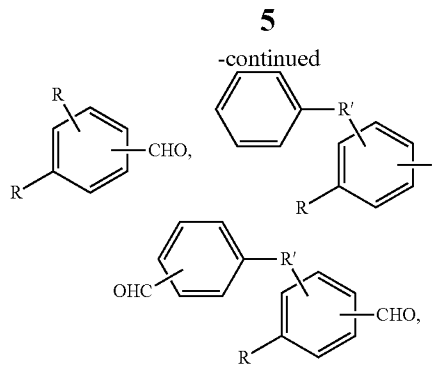

in which R and R' have the meanings already given.

A "primary amino group" refers to an amino group which is bonded to a single organic radical and bears two hydrogen atoms; a "secondary amino group" refers to an amino group which is bonded to two organic radicals which may also together be part of a ring and bears one hydrogen atom; and a "tertiary amino group" refers to an amino group which is bonded to three organic radicals, two or three of which may also be part of one or more rings, and does not bear any hydrogen atom.

A "primary diamine" refers to a compound having two primary amino groups.

"Aromatic" refers to an amine or an isocyanate, the amino or isocyanate groups of which are bonded directly to an aromatic carbon atom.

"Aliphatic" refers to an amine or an isocyanate, the amino or isocyanate groups of which are bonded directly to an aliphatic carbon atom.

A "silane group" refers to a silyl group bonded to an organic radical and having one to three, especially two or three, hydrolyzable alkoxy radicals on the silicon atom.

"Molecular weight" refers to the molar mass (in g/mol) of a molecule or a molecule residue. "Average molecular weight" refers to the number-average molecular weight ($M_n$) of a polydisperse mixture of oligomeric or polymeric molecules or molecule residues. It is typically determined by means of gel permeation chromatography (GPC) against polystyrene as standard.

A dotted line in the formulae in each case represents the bond between a substituent and the corresponding molecular radical.

Substance names beginning with "poly", such as polyamine, polyol or polyisocyanate, refer to substances containing, in a formal sense, two or more of the functional groups that occur in their name per molecule.

A substance or composition is referred to as "storage-stable" or "storable" when it can be stored at room temperature in a suitable container over a prolonged period, typically over at least 3 months to up to 6 months or more, without any change in its application or use properties to a degree of relevance for the use thereof as a result of the storage.

"Room temperature" refers to a temperature of 23° C.

"Plasticizers" refer to liquid or dissolved substances which are not chemically incorporated within a cured polymer and typically exert a plasticizing effect on the polymer.

The aldehyde mixture of the use according to the invention especially is a reaction product of a formylation of at least one alkylbenzene of the formula

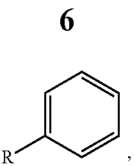

In which R has the meanings already described.

In this connection, the reaction product was especially not purified or only purified insofar as both the main constituent—the described aldehydes of the formula (I)—through the purification process, such as, for example, extraction or especially distillation or fractionation, and the secondary constituent—the described alkylbenzene compounds not corresponding to the formula (I), which represent byproducts of the formylation—to the greatest possible extent remain in the reaction product and are not separated from one another. Such a reaction product is also referred to below as "crude product".

The formylation is preferably carried out with carbon monoxide (CO) as formylation reagent.

The formylation of the alkylbenzene is preferably carried out with carbon monoxide in the presence of hydrofluoric acid and boron trifluoride ($HF-BF_3$ or $HBF_4$) as acid catalyst. This process is particularly advantageous since it is feasible under mild conditions and accordingly proceeds particularly selectively. With its high vapor pressure, the catalyst can be easily separated and used again, by which an expensive purification and waste disposal as with other catalyst systems is avoided.

The reaction is preferably carried out at a partial carbon monoxide pressure of 5 to 50 bar, especially 10 to 30 bar, and a temperature of −50 to +20° C., especially −30 to 0° C.

The molar ratio of alkylbenzene to HF to $BF_3$ is preferably in the range from 1 to (2.5 to 30) to (1 to 5), especially 1 to (3 to 25) to (1.1 to 3).

The reaction product is preferably added to a mixture of ice and water, and extracted using a solvent, especially an alkane, such as hexane or heptane. The extract is subsequently preferably freed from traces of acid by washing with water or especially an aqueous base, for example an aqueous sodium hydroxide solution, and the solvent and optionally additional low-molecular-weight constituents present are subsequently removed by distillation from the reaction mixture.

The crude product thus obtained is optionally clarified or lightened in color with a suitable method, for example by means of filtration or adsorption. An additional purification of the crude product thus obtained, especially a distillation or fractionation of the aldehydes of the formula (I), is dispensed with, which is particularly advantageous with regard to production expenditure and costs.

The aldehyde mixture preferably contains a content of aldehydes of the formula (I) in the range from 80% to 95% by weight and a content of alkylbenzene compounds not corresponding to the formula (I) of 5% to 20% by weight.

The aldehyde mixture is preferably free from low-molecular-weight constituents and accordingly odorless. Especially, the aldehyde mixture is free from solvents, benzaldehyde and $C_{1-5}$-alkylbenzaldehydes.

The aldehyde mixture is preferably light in color.

Especially, it has a Gardner color standard number according to DIN ISO 4630 of at most 12, preferably as most 10. Latent hardeners obtained with that are also suitable for light-colored polyurethane compositions.

Preferably, the amine to be blocked by the use according to the invention has at least one primary or secondary amino group.

Particularly preferably, the amine to be blocked has at least one primary or secondary amino group and additionally at least one reactive group selected from primary amino group, secondary amino group, hydroxyl group and silane group.

Such an amine is suitable as latent hardener and/or crosslinking agent and/or adhesion promoter for compounds with reactive groups, such as, especially, isocyanate groups. In blocked form, with exclusion of moisture, it does not react or reacts only very slowly with such compounds, while, on contact with moisture, it can react with hydrolysis.

Suitable amines for the blocking are especially selected from the group consisting of primary aliphatic diamines, primary aromatic diamines, primary aliphatic triamines, aliphatic diamines having a primary and a secondary amino group, aliphatic polyamines having two primary and a secondary amino group, aminoalcohols, dialkanolamines, aminosilanes and alkanolaminosilanes.

Suitable primary aliphatic diamines are especially 1,2-ethanediamine, 1,2-propanediamine, 1,3-propanediamine, 1,4-butanediamine, 1,3-butanediamine, 2-methyl-1,2-propanediamine, 1,3-pentanediamine, 1,5-pentanediamine, 2,2-dimethyl-1,3-propanediamine, 1,6-hexanediamine, 1,5-diamino-2-methylpentane, 1,7-heptanediamine, 1,8-octanediamine, 2,5-dimethyl-1,6-hexanediamine, 1,9-nonanediamine, 2,2(4),4-trimethyl-1,6-hexanediamine, 1,10-decanediamine, 1,11-undecanediamine, 2-butyl-2-ethyl-1,5-pentanediamine, 1,12-dodecanediamine, 1,2-cyclohexanediamine, 1,3-cyclohexanediamine, 1,4-cyclohexanediamine, 1-amino-3-aminomethyl-3,5,5-trimethylcyclohexane, 4(2)-methyl-1,3-cyclohexanediamine, 1,3-bis(aminomethyl)cyclohexane, 1,4-bis(aminomethyl)cyclohexane, bis(4-aminocyclohexyl)methane, bis(4-amino-3-methylcyclohexyl)methane, bis(4-amino-3-ethylcyclohexyl)methane, bis(4-amino-3,5-dimethylcyclohexyl)methane, bis(4-amino-3-ethyl-5-methylcyclohexyl)methane, 2,5(2,6)-bis(aminomethyl)bicyclo[2.2.1]heptane, 3(4),8(9)-bis(aminomethyl)tricyclo[5.2.1.$0^{2,6}$]decane, 1,3-bis(aminomethyl)benzene, 1,4-bis(aminomethyl)benzene, 3-oxa-1,5-pentanediamine, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine, am-polyoxypropylenediamine having an average molecular weight in the range from 200 to 4000 g/mol, especially the Jeffamine® products D-230, D-400, XTJ-582, D-2000, XTJ-578 or D-4000 (all from Huntsman), α,ω-polyoxypropylene/polyoxyethylenediamine, especially the Jeffamine® products ED-600, ED-900, ED-2003 or HK-511 (all from Huntsman), α,ω-polyoxypropylene/polyoxy-1,4-butylenediamine, especially the Jeffamine® products THF-100, THF-140, THF-230, XTJ-533 or XTJ-536 (all from Huntsman), α,ω-polyoxypropylen/polyoxy-1,2-butylenediamine, especially the Jeffamine® products XTJ-568 or XTJ-569 (both from Huntsman) or α,ω-polyoxy-1,2-butylenediamine, especially Jeffamine® XTJ-523 (from Huntsman).

Suitable primary aromatic diamines are especially 1,3-phenylenediamine, 1,4-phenylenediamine, 4(2)-methyl-1,3-phenylenediamine (TDA), 3,5-diethyl-2,4(6)-toluylenediamine (DETDA) or 4,4'-diaminodiphenylmethane (MDA).

Suitable primary aliphatic triamines are especially 1,3,6-triaminohexane, 1,4,8-triaminooctane, 4-aminomethyl-1,8-octanediamine, 5-aminomethyl-1,8-octanediamine, 1,6,11-triaminoundecane, 1,3,5-triaminocyclohexane, 1,3,5-tris(am inomethyl)cyclohexane, 1,3,5-tris(aminomethyl)benzene, trim ethylolpropane- or glycerol-started tris(w-polyoxypropylenamine) having an average molecular weight in the range from 380 to 6000 g/mol, especially the Jeffamine® products T-403, T-3000 or T-5000 (all from Huntsman), or trimethylolpropane-started tris(w-polyoxypropylene/polyoxy-1,2-butylenamine), especially Jeffamine® XTJ-566 (from Huntsman).

Suitable aliphatic diamines having a primary and a secondary amino group are especially N-methyl-1,2-ethanediamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, N-benzyl-1,2-ethanediamine, 4-am inomethylpiperidine, 3-(4-aminobutyl)piperidine, N-(2-aminoethyl)piperazine, N-(2-aminopropyl)piperazine, N-benzyl-1,2-propanediamine, N-benzyl-1,3-propanediamine, N-methyl-1,3-propanediamine, N-ethyl-1,3-propanediamine, N-butyl-1,3-propanediamine, N-hexyl-1,3-propanediamine, N-(2-ethylhexyl)-1,3-propanediamine, N-dodecyl-1,3-propanediamine, N-cyclohexyl-1,3-propanediamine, 3-methylamino-1-pentylamine, 3-ethylamino-1-pentylamine, 3-butylamino-1-pentylamine, 3-hexylamino-1-pentylamine, 3-(2-ethylhexyl)amino-1-pentylamine, 3-dodecylamino-1-pentylamine, 3-cyclohexylamino-1-pentylamine, fatty diamines, such as N-cocoalkyl-1,3-propanediamine, N-oleyl-1,3-propanediamine, N-soyaalkyl-1,3-propanediamine, N-tallowalkyl-1,3-propanediamine or N—($C_{16-22}$-alkyl)-1,3-propanediamine, such as, for example, available under the Duomeen® trade name from Akzo Nobel, or products from the Michael-type addition of aliphatic primary diamines to acrylonitrile, maleic or fumaric acid diesters, citraconic acid diesters, (meth)acrylic acid esters, (meth)acrylamides or itaconic acid diesters, reacted in the molar ratio 1:1.

Suitable aliphatic polyamines having two primary and a secondary amino group are especially bis(hexamethylene)triamine (BHMT), diethylenetriamine (DETA), dipropylenetriamine (DPTA), N-(2-aminoethyl)-1,3-propanediamine (N3-Amin), N3-(3-aminopentyl)-1,3-pentanediamine or N5-(3-amino-1-ethylpropyl)-2-methyl-1,5-pentanediamine.

Suitable aminoalcohols are especially 2-aminoethanol, 2-amino-1-propanol, 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol or higher homologs thereof, 4-(2-aminoethyl)-2-hydroxyethylbenzene, 3-aminomethyl-3,5,5-trimethylcyclohexanol, derivatives bearing a primary amino group of glycols, such as diethylene glycol, dipropylene glycol, dibutylene glycol or higher oligomers or polymers of these glycols, especially 2-(2-aminoethoxy)ethanol, 2-(2-(2-aminoethoxy)ethoxy)ethanol or α-(2-hydroxymethylethyl)-ω-(2-aminomethylethoxy)poly(oxy(methyl-1,2-ethanediyl), 3-(2-hydroxyethoxy)propylamine, 3-(2-(2-hydroxyethoxy)ethoxy)propylamine or 3-(6-hydroxyhexyloxy)propylamine, N-methylethanolamine, N-ethylethanolamine, N-(n-propyl)ethanolamine, N-isopropylethanolamine, N-(n-butyl)ethanolamine, N-isobutylethanolamine, N-(2-butyl)ethanolamine, N-(tert-butyl)ethanolamine, N-hexylethanolamine, N-isohexylethanolamine or N-(2-ethylhexyl)ethanolamine, and also N-(2-aminoethyl)ethanolamine or reaction products of primary aliphatic diamines such as the abovementioned with monoepoxides in the molar ratio 1:1, especially the reaction product of a superstoichiometric amount of 1,2-propanediamine or 2-methyl-1,5-pentanediamine with cresyl glycidyl ether and subsequent removal of unreacted 1,2-propanediamine or 2-methyl-1,5-pentanediamine; furthermore, polyvalent aminoalcohols, especially N,N'-dialkoxylation products of the primary aliphatic diamines mentioned, such as, for example, Jeffamine® C-346 (from Huntsman), or N,N'-diadducts of the primary aliphatic diamines mentioned with monoglycidyl ethers, such as especially phenyl glycidyl ether, cresyl glycidyl ether, tert-butylphenyl glycidyl ether, cardanol glycidyl ether or 2-ethylhexyl glycdiyl ether, or α,ω-diadducts of diglycidyl ethers, such as especially butanediol diglycidyl ether, hexanediol diglycidyl ether, dipropylene glycol diglycidyl ether, polypropylene glycol diglycidyl ether, bisphenol A diglycidyl ether or bisphenol F diglycidyl ether, with monoamines, such as especially isopropylamine, n-butylamine, isobutylamine, 2-butylamine, tert-butylamine, n-hexylamine, isohexylamine, 2-ethylhexylamine or benzylamine.

Suitable dialkanolamines are especially diethanolamine, diisopropanolamine or 2-amino-2-ethyl-1,3-propandiol.

Suitable am inosilanes are especially 3-am inopropyltrimethoxysilane, 3-aminopropyltriethoxysilane or 3-am inopropyldimethoxymethylsilane.

Suitable alkanolaminosilanes are especially alkoxylates or adducts of the aminosilanes mentioned with epoxides, such as especially ethylene oxide, propylene oxide, phenyl glycidyl ether, cresyl glycidyl ether or an alkyl glycidyl ether, or an epoxysilane, such as especially 3-glycidoxypropyltrimethoxysilane or 3-glycidoxypropyltriethoxysilane.

Preferred amines for the blocking are primary aliphatic diamines, primary aliphatic triamines or dialkanolamines.

Particularly preferred amines for the blocking are selected from the group consisting of diethanolamine, 1,6-hexanediamine, 1-amino-3-aminomethyl-3,5,5-trimethylcyclohexane, 4(2)-methyl-1,3-cyclohexanediamine, 1,3-bis(aminomethyl)cyclohexane, 1,4-bis(aminomethyl)cyclohexane, 1,3-bis(aminomethyl)benzene, 1,2-cyclohexanediamine, 1,3-cyclohexanediamine, 1,4-cyclohexanediamine, bis(4-aminocyclohexyl)methane, 2,5(2,6)-bis(aminomethyl)bicyclo[2.2.1]heptane, 3(4),8(9)-bis(aminomethyl)tricyclo[5.2.1.0$^{2,6}$]decane, α,ω-polyoxypropylenediamine having an average molecular weight in the range from 200 to 4000 g/mol, especially the Jeffamine® products D-230, D-400, XTJ-582, D-2000, XTJ-578 or D-4000 (all from Huntsman), and trimethylolpropane- or glycerol-started tris(w-polyoxypropylenamine) having an average molecular weight in the range from 380 to 6000 g/mol, especially the Jeffamine® products T-403, T-3000 or T-5000 (all from Huntsman).

Preferred from them is diethanolamine, 1,6-hexanediamine, 1-amino-3-aminomethyl-3,5,5-trimethylcyclohexane, 1,3-bis(aminomethyl)benzene, α,ω-polyoxypropylenediamine having an average molecular weight of approximately 240 g/mol or trimethylolpropane-started tris (w-polyoxypropylenamine) having an average molecular weight of approximately 440 g/mol.

These amines are readily available, in blocked form of low viscosity, and make possible polyurethane compositions with good storage stability, good processability, fast curing with a moderate open time and excellent mechanical properties, especially surprisingly high strength with high extensibility.

In the use according to the invention of the aldehyde mixture, the aldehyde mixture is preferably reacted with the amine to be blocked so that the aldehyde mixture is combined with the amine to give a reaction mixture, optionally with addition of a solvent, the aldehyde groups being present, with regard to the primary and secondary amino groups, preferably stoichiometricaly or in stoichiometric excess, and the condensation water produced in the reaction and optionally solvent used during or after the combining are removed from the reaction mixture using a suitable method, optionally with heating of it and/or application of vacuum. The condensation water is preferably removed from the heated reaction mixture by means of application of vacuum, without solvent being used there.

The reaction is preferably carried out at a temperature in the range from 20° C. to 120° C., especially 40° C. to 100° C.

Optionally, a catalyst is used in the reaction, especially an acid catalyst.

A further subject of the invention is a blocked amine obtained from the use according to the invention of the aldehyde mixture described.

The blocked amine especially has functional groups of the formulae (II) and/or (III),

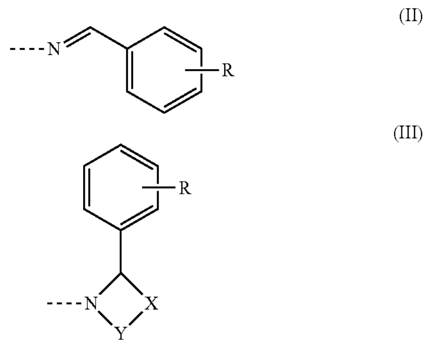

in which

X is O or S or NR$^0$, in which R$^0$ is a monovalent organic radical having 1 to 18 carbon atoms, Y is a 1,2-ethylene or 1,3-propylene radical, which is optionally substituted, and R has the meanings already described.

Preferably, in the functional group of the formula (II) or (III), R is in the meta or para position, in particular in the para position.

The functional group of the formula (II) results from the condensation reaction of a primary amino group with an aldehyde of the formula (I). It represents an aldimino group.

The functional group of the formula (III) results from the condensation reaction of a grouping of the formula —NH—Y—XH with an aldehyde of the formula (I), Y and X having the meanings already mentioned.

Preferably, R$^0$ is an alkyl, cycloalkyl or arylalkyl radical having 1 to 18 carbon atoms, which optionally bears one or two groups selected from carboxylic acid ester, nitrile, nitro, phosphonic acid ester, sulfone and sulfonic acid ester groups.

Preferably, X is O.

Preferably, NH and XH are separated from one another by two carbon atoms. Such a functional group of the formula (III) represents an oxazolidino group. It is especially reactive when used as latent hardener in polyurethane compositions.

Preferably, Y is a 1,2-ethylene or 1,3-propylene or 1,2-propylene radical or is a 3-alkyloxy-1,2-propylene or 3-aryloxy-1,2-propylene radical, the last two radicals being optionally substituted and optionally having a silane group, or can, in the case of n=1 and X═O, also be a radical of the formula

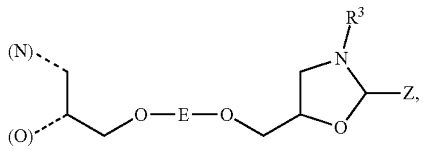

in which E is a divalent hydrocarbon radical having 6 to 20 carbon atoms which optionally bears one or more ether, ester or glycidoxy groups, and $R^3$ is an alkyl, cycloalkyl or aralkyl radical having 1 to 35 carbon atoms which optionally bears one or more ether groups.

Particularly preferably, X is O and Y is 1,2-ethylene or an optionally substituted 3-alkyloxy-1,2-propylene or 3-aryloxy-1,2-propylene radical.

Preferably, $R^3$ is methyl, ethyl, n-propyl, isopropyl, n-butyl, isobutyl, 2-butyl, tert-butyl, n-hexyl, isohexyl, 2-ethylhexyl, dodecyl, benzyl or a methoxy-terminated polyoxypropylene radical, which can also contain oxyethylene fractions.

Preferably, E is 4,4'-methylenediphenyl, 4,4'-(2,2-propylene)diphenyl, 1,2- or 1,3- or 1,4-phenyl, 1,4-butylene, 1,6-hexylene or $\alpha,\omega$-polyoxypropylene having an average molecular weight in the range from 96 to 1000 g/mol.

The blocked amine can advantageously be used as a latent hardener and/or crosslinking agent and/or adhesion promoter.

For use as adhesion promoter, the blocked amine preferably comprises at least one silane group. The adhesion promoter is especially useful for employment in compositions containing isocyanate and/or silane groups.

Preferably, the blocked amine is used as latent hardener for compositions which comprise reactive groups which can react with amine hydrogens, such as especially isocyanate groups or epoxy groups. For this use, the blocked amine comprises, besides functional groups of the formulae (II) and/or (III), preferably at least one additional reactive group selected from the group consisting of functional groups of the formulae (II) and/or (III), hydroxyl groups, mercapto groups, primary amino groups and secondary amino groups.

Preference is given to latent hardeners which have two or three functional groups of the formula (II), which thus represent dialdimines or trialdimines. Furthermore preferred are latent hardeners which have a functional group of the formula (II) and a hydroxyl group or primary amino group or secondary amino group, in particular a hydroxyl group, which thus represent hydroxyaldimines or aminoaldimines.

Furthermore preferred are latent hardeners which have a functional group of the formula (II) and a functional group of the formula (III) and represent especially aldimino-oxazolidines.

Furthermore preferred are latent hardeners which have two functional groups of the formula (III) and represent especially bisoxazolidines.

Furthermore preferred are latent hardeners which have a functional group of the formula (III) and a hydroxyl group and represent especially hydroxyoxazolidines.

Particularly preferred are dialdimines, trialdimines, hydroxyaldimines, bisoxazolidines and hydroxyoxazolidines.

The most preferred are dialdimines and trialdimines, especially dialdimines.

Latent hardeners, which contain a free OH or NH group, react on mixing with polyisocyanates to give reaction products containing isocyanate groups, these for their part representing latent hardeners and acting, on admission of moisture, as crosslinking agents.

In the case where diethanolamine is used as amine to be blocked, a hydroxyoxazolidine of the formula

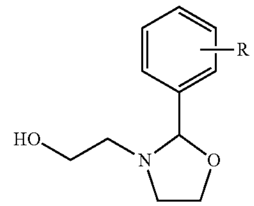

is obtained.

Such hydroxyoxazolidines are especially suitable for the reaction with a diisocyanate or with a carbonate to give a bisoxazolidine of the formula

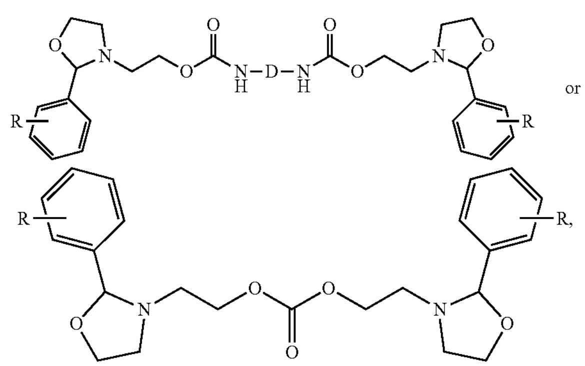

in which D is a divalent hydrocarbon radical having 6 to 15 carbon atoms, especially 1,6-hexamethylene or (1,5,5-trimethylcyclohexan-1-yl)methane-1,3 or 4(2)-methyl-1,3-phenylene, and R has the meanings already described.

The latent hardeners are especially suitable for compositions containing isocyanate groups, especially polyurethane compositions.

The latent hardener has, besides functional groups of the formulae (II) and/or (III), fractions of additional functional groups from condensation reactions, with amino groups, of the alkylbenzene compounds not corresponding to the formula (I). These fractions surprisingly do not harm the use of the latent hardener, but even bestow advantages. Thus, the latent hardeners are of lower viscosity and have a lower crystallization temperature than corresponding latent hardeners, for the preparation of which a purified blocking agent in the form of pure aldehydes of the formula (I) was used, and result in polyurethane compositions of even greater strengths, without this adversely impacting the storage stability.

An additional subject of the invention is a composition containing isocyanate groups comprising at least one blocked amine obtained from the use described.

Preferably, the composition containing isocyanate groups comprises:

at least one polyisocyanate and/or at least one polyurethane polymer containing isocyanate groups, and at least one polyaldimine of the formula (IV),

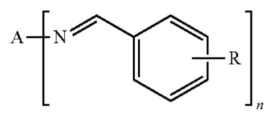

(IV)

in which n is 2 or 3,

A is an n-valent organic radical having a molecular weight in the range from 28 to 10 000 g/mol, and R has the meanings already described.

Preferably, R is in the meta or para position, especially in the para position.

Preferably, A is an n-valent hydrocarbon radical having a molecular weight in the range from 28 to 6000 g/mol, which optionally has one or more groups selected from ether, ester, carbonate, urethane and urea groups.

Preferably, n is 2.

Preferably, A is an n-valent aliphatic, cycloaliphatic or arylaliphatic hydrocarbon radical optionally having ether oxygen and having a molecular weight in the range from 28 to 6000 g/mol. Such polyaldimines based on aliphatic amines are particularly advantageous in toxicological terms.

Particularly preferably, A is 1,6-hexylene, (1,5,5-trimethylcyclohexan-1-yl)methane-1,3, 4(2)-methyl-1,3-cyclohexylene, 1,3-cyclohexylenebis(methylene), 1,4-cyclohexylenebis(methylene), 1,3-phenylenebis(methylene), 1,2-cyclohexylene, 1,3-cyclohexylene, 1,4-cyclohexylene, methylenebis(2-methylcyclohexan-4-yl), (bicyclo[2.2.1]heptan-2,5(2,6)-diyl)dimethylene, (tricyclo[5.2.1.0$^{2,6}$]decan-3(4),8(9)-diyl)dimethylene, $\alpha,\omega$-polyoxypropylene having an average molecular weight in the range from 170 to 4000 g/mol and trimethylolpropane- or glycerol-started tris(w-polyoxypropylene) having an average molecular weight in the range from 330 to 6000 g/mol.

A is especially selected from the group consisting of 1,6-hexylene, (1,5,5-trimethylcyclohexan-1-yl)methane-1,3, 1,3-cyclohexylenebis(methylene), 1,3-phenylenebis (methylene), $\alpha,\omega$-polyoxypropylene having an average molecular weight in the range from 170 to 470 g/mol and trimethylolpropane-started tris(w-polyoxypropylene) having an average molecular weight in the range from 330 to 450 g/mol.

Such polyaldimines are especially readily available, of low viscosity at room temperature, and make possible compositions having good mechanical properties, especially high strength and high extensibility.

A suitable polyisocyanate is especially a commercially available polyisocyanate, especially

- aromatic di- or triisocyanates, preferably diphenylmethane 4,4'- or 2,4'- or 2,2'-diisocyanate or any mixtures of these isomers (MDI), toluylene 2,4- or 2,6-diisocyanate or any mixtures of these isomers (TDI), mixtures of MDI and MDI homologs (polymeric MDI or PMDI), phenylene 1,3- or 1,4-diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODD, dianisidine diisocyanate (DADI), tris(4-isocyanatophenyl)methane or tris(4-isocyanatophenyl) thiophosphate; preferably MDI or TDI;
- aliphatic, cycloaliphatic or arylaliphatic di- or triisocyanates, preferably tetramethylene 1,4-diisocyanate, 2-methylpentamethylene 1,5-diisocyanate, hexamethylene 1,6-diisocyanate (HDI), 2,2,4- and/or 2,4,4-trimethylhexamethylene 1,6-diisocyanate (TMDI), decamethylene 1,10-diisocyanate, dodecamethylene 1,12-diisocyanate, lysine diisocyanate or lysine ester diisocyanate, cyclohexane 1,3- or 1,4-diisocyanate, 1-methyl-2,4- and/or -2,6-diisocyanatocyclohexane ($H_6$TDI), 1-isocyanato-3,3,5-trimethyl-5-isocyanatomethylcyclohexane (IPDI), perhydrodiphenylmethane 2,4'- and/or 4,4'-diisocyanate ($H_{12}$MDI), 1,3- or 1,4-bis(isocyanatomethyl)cyclohexane, m- or p-xylylene diisocyanate, tetramethylxylylene 1,3- or 1,4-diisocyanate, 1,3,5-tris(isocyanatomethyl)benzene, bis(1-isocyanato-1-methylethyl)naphthalene, dimer or trimer fatty acid isocyanates, such as, especially, 3,6-bis(9-isocyanatononyl)-4,5-di(1-heptenyl)cyclohexene (dimeryl diisocyanate); preferably $H_{12}$MDI or HDI or IPDI;
- oligomers or derivatives of the di- or triisocyanates mentioned, especially derived from HDI, IPDI, MDI or TDI, especially oligomers containing uretdione or isocyanurate or iminooxadiazinedione groups or various groups among these; or di- or polyfunctional derivatives containing ester or urea or urethane or biuret or allophanate or carbodiimide or uretonimine or oxadiazinetrione groups or various groups among these. In practice, polyisocyanates of this kind are typically mixtures of substances having different degrees of oligomerization and/or chemical structures. They especially have an average NCO functionality of 2.1 to 4.0.

Preference is given, as polyisocyanate, to aliphatic, cycloaliphatic or aromatic diisocyanates, especially HDI, IPDI, $H_{12}$MDI, TDI or MDI, especially HDI, IPDI, TDI or MDI.

A suitable polyurethane polymer containing isocyanate groups is especially obtained from the reaction of at least one polyol with a superstoichiometric amount of at least one polyisocyanate. The reaction is preferably carried out with exclusion of moisture at a temperature in the range from 50 to 160° C., optionally in the presence of suitable catalysts. The NCO/OH ratio is preferably in the range from 1.3/1 to 2.5/1. The polyisocyanate remaining in the reaction mixture after the conversion of the OH groups, especially monomeric diisocyanate, can be removed, especially by means of distillation, which is preferable in the case of a high NCO/OH ratio. The polyurethane polymer obtained preferably has a content of free isocyanate groups in the range from 0.5% to 10% by weight, especially 1% to 5% by weight, especially preferably 1% to 3% by weight. The polyurethane polymer can optionally be prepared with additional use of plasticizers or solvents, in which case the plasticizers or solvents used do not contain any groups reactive toward isocyanates.

Preference is given, as polyisocyanate for the preparation of a polyurethane polymer containing isocyanate groups, to the polyisocyanates already mentioned, especially the diisocyanates, preferably MDI, TDI, IPDI or HDI.

Suitable polyols are commercial polyols or mixtures thereof, especially

- polyether polyols, especially polyoxyalkylene diols and/or polyoxyalkylenetriols, especially polymerization products of ethylene oxide or 1,2-propylene oxide or 1,2- or 2,3-butylene oxide or oxetane or tetrahydrofuran or mixtures thereof, where these may be polymerized with the aid of a starter molecule having two or more active hydrogen atoms, especially a starter molecule such as water, ammonia or a compound having multiple OH or NH groups, such as, for example, 1,2-ethanediol, 1,2- or 1,3-propanediol, neopentyl glycol, diethylene glycol, triethylene glycol, the isomeric dipropylene glycols or tripropylene glycols, the isomeric butanediols, pentanediols, hexanediols, heptanediols, octanediols, nonanediols, decanediols, undecanediols, 1,3- or 1,4-cyclohexanedimethanol, bisphenol A, hydrogenated bisphenol A, 1,1,1-trimethylolethane, 1,1,1-trimethylolpropane, glycerol or aniline, or mixtures of the abovementioned compounds. Likewise suitable are polyether polyols with polymer particles dispersed therein, especially those with styrene/acrylonitrile (SAN) particles or polyurea or polyhydrazodicarbonamide (PHD) particles.

Preferred polyether polyols are polyoxypropylene diols or polyoxypropylene triols, or what are called ethylene oxide-terminated (EO-endcapped) polyoxypropylene diols or triols. The latter are mixed polyoxyethylene/polyoxypropylene polyols which are especially obtained in that polyoxypropylene diols or triols, on conclusion of the polypropoxylation reaction, are further alkoxylated with ethylene oxide and thereby eventually have primary hydroxyl groups.

Preferred polyether polyols have a degree of unsaturation of less than 0.02 meq/g, especially less than 0.01 meq/g.

Polyester polyols, also called oligoesterols, prepared by known processes, especially the polycondensation of hydroxycarboxylic acids or lactones or the polycondensation of aliphatic and/or aromatic polycarboxylic acids with di- or polyhydric alcohols. Preference is given to polyester diols from the reaction of dihydric alcohols, such as, especially, 1,2-ethanediol, diethylene glycol, 1,2-propanediol, dipropylene glycol, 1,4-butanediol, 1,5-pentanediol, 1,6-hexanediol, neopentyl glycol, glycerol, 1,1,1-trimethylolpropane or mixtures of the abovementioned alcohols, with organic dicarboxylic acids or the anhydrides or esters thereof, such as, especially, succinic acid, glutaric acid, adipic acid, suberic acid, sebacic acid, dodecanedicarboxylic acid, maleic acid, fumaric acid, phthalic acid, isophthalic acid, terephthalic acid or hexahydrophthalic acid or mixtures of the abovementioned acids, or polyester polyols from lactones, such as, especially, ε-caprolactone. Particular preference is given to polyester polyols from adipic acid or sebacic acid or dodecanedicarboxylic acid and hexanediol or neopentyl glycol.

Polycarbonate polyols as obtainable by reaction, for example, of the abovementioned alcohols—used to form the polyester polyols—with dialkyl carbonates, diaryl carbonates or phosgene.

Block copolymers bearing at least two hydroxyl groups and having at least two different blocks having polyether, polyester and/or polycarbonate structure of the type described above, especially polyether polyester polyols.

Polyacrylate polyols and polymethacrylate polyols.

Polyhydroxy-functional fats and oils, for example natural fats and oils, especially castor oil; or polyols obtained by chemical modification of natural fats and oils—called oleochemical polyols—for example the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes, such as alcoholysis or ozonolysis, and subsequent chemical linkage, for example by transesterification or dimerization, of the degradation products or derivatives thereof thus obtained. Suitable degradation products of natural fats and oils are especially fatty acids and fatty alcohols and also fatty acid esters, especially the methyl esters (FAME), which can be derivatized to hydroxy fatty acid esters by hydroformylation and hydrogenation, for example.

Polyhydrocarbon polyols, also called oligohydrocarbonols, such as, for example, polyhydroxy-functional polyolefins, polyisobutylenes, polyisoprenes; polyhydroxy-functional ethylene/propylene, ethylene/butylene or ethylene/propylene/diene copolymers, as produced, for example, by Kraton Polymers; polyhydroxy-functional polymers of dienes, especially of 1,3-butadiene, which can especially also be prepared from anionic polymerization; polyhydroxy-functional copolymers of dienes, such as 1,3-butadiene, or diene mixtures and vinyl monomers, such as styrene, acrylonitrile, vinyl chloride, vinyl acetate, vinyl alcohol, isobutylene and isoprene, for example polyhydroxy-functional acrylonitrile/butadiene copolymers, as can be prepared, for example, from epoxides or aminoalcohols and carboxyl-terminated acrylonitrile/butadiene copolymers (commercially available, for example, under the Hypro® CTBN or CTBNX or ETBN name from Emerald Performance Materials); and hydrogenated polyhydroxy-functional polymers or copolymers of dienes.

Also especially suitable are mixtures of polyols.

Preference is given to polyether polyols, polyester polyols, polycarbonate polyols, poly(meth)acrylate polyols or polybutadiene polyols.

Particular preference is given to polyether polyols, polyester polyols, especially aliphatic polyester polyols, or polycarbonate polyols, especially aliphatic polycarbonate polyols.

The most preferred are polyether polyols, especially polyoxypropylene di- or triols or ethylene oxide-terminated polyoxypropylene di- or triols.

Preference is given to polyols having an average molecular weight in the range from 400 to 20 000 g/mol, preferably from 1000 to 15 000 g/mol.

Preference is given to polyols having an average OH functionality in the range from 1.6 to 3.

Preference is given to polyols that are liquid at room temperature.

In the preparation of a polyurethane polymer containing isocyanate groups, it is also possible to use fractions of di- or polyfunctional alcohols, especially 1,2-ethanediol, 1,2-propanediol, 1,3-propanediol, 2-methyl-1,3-propanediol, 1,2-butanediol, 1,3-butanediol, 1,4-butanediol, 1,3-pentanediol, 1,5-pentanediol, 3-methyl-1,5-pentanediol, neopentyl glycol, dibromoneopentyl glycol, 1,2-hexanediol, 1,6-hexanediol, 1,7-heptanediol, 1,2-octanediol, 1,8-octanediol, 2-ethyl-1,3-hexanediol, diethylene glycol, triethylene glycol, dipropylene glycol, tripropylene glycol, 1,3- or 1,4-cyclohexanedimethanol, ethoxylated bisphenol A, propoxylated bisphenol A, cyclohexanediol, hydrogenated bisphenol A, dimer fatty acid alcohols, 1,1,1-trimethylolethane, 1,1,1-trimethylolpropane, glycerol, pentaerythritol, sugar alcohols, such as especially xylitol, sorbitol or mannitol, or sugars, such as especially sucrose, or alkoxylated derivatives of the alcohols mentioned or mixtures of the alcohols mentioned.

The polyurethane polymer containing isocyanate groups preferably has an average molecular weight in the range from 1500 to 20 000 g/mol, especially 2000 to 15 000 g/mol. It is preferably liquid at room temperature.

For the use in a hot-melt adhesive, a polyurethane polymer which is solid at room temperature is preferred, which polymer is prepared starting from at least one polyol which is solid at room temperature. A suitable polymer which is solid at room temperature is crystalline, partially crystalline or amorphous at room temperature. Its melting point is preferably in the range from 50 to 180° C., especially 70 to 150° C. Preference is given to polyester polyols, especially those derived from hexanediol and adipic acid or dodecanedioic acid, or acrylate polyols. The polyurethane polymer is especially prepared at a temperature above the melting point of the polymer which is solid at room temperature.

The composition preferably comprises at least one polyurethane polymer containing isocyanate groups.

In addition to a polyurethane polymer comprising isocyanate groups, the composition can furthermore contain at least one diisocyanate and/or one oligomer or polymer of a diisocyanate, especially an IPDI isocyanurate or a TDI oligomer or a mixed isocyanurate based on TDI/HDI or an HDI oligomer or a form of MDI which is liquid at room temperature.

A form of MDI which is liquid at room temperature is either 4,4'-MDI liquefied by partial chemical modification—especially carbodiimidization or uretonimine formation or adduct formation with polyols—or it is a mixture of 4,4'-MDI with other MDI isomers (2,4'-MDI and/or 2,2'-MDI), and/or MDI oligomers and/or MDI homologs (PMDI), that has been brought about selectively by blending or results from the production process.

Preferably, the composition comprises, besides at least one polyisocyanate and/or polyurethane polymer comprising isocyanate groups and at least one polyaldimine of the formula (IV) and additionally one or more further constituents which are especially selected from catalysts, fillers, plasticizers and solvents.

Suitable catalysts are especially catalysts for the hydrolysis of aldimino groups, especially organic acids, especially carboxylic acids, such as 2-ethylhexanoic acid, lauric acid, stearic acid, isostearic acid, oleic acid, neodecanoic acid, benzoic acid, salicylic acid or 2-nitrobenzoic acid, organic carboxylic acid anhydrides, such as phthalic anhydride, hexahydrophthalic anhydride or methylhexahydrophthalic anhydride, silyl esters of carboxylic acids, organic sulfonic acids, such as methanesulfonic acid, p-toluenesulfonic acid or 4-dodecylbenzenesulfonic acid, sulfonic acid esters, other organic or inorganic acids, or mixtures of the abovementioned acids and acid esters. Particular preference is given to carboxylic acids, especially aromatic carboxylic acids, such as benzoic acid, 2-nitrobenzoic acid or especially salicylic acid.

Suitable catalysts are furthermore catalysts for the acceleration of the reaction of isocyanate groups, especially organotin(IV) compounds, such as especially dibutyltin diacetate, dibutyltin dilaurate, dibutyltin dichloride, dibutyltin diacetylacetonate, dimethyltin dilaurate, dioctyltin diacetate, dioctyltin dilaurate or dioctyltin diacetylacetonate, complexes of bismuth(III) or zirconium(IV), especially with ligands selected from alkoxides, carboxylates, 1,3-diketonates, oxinate, 1,3-ketoesterates and 1,3-ketoamidates, or compounds containing tertiary amino groups, such as especially 2,2'-dimorpholinodiethyl ether (DMDEE).

Also especially suitable are combinations of different catalysts.

Suitable fillers are especially ground or precipitated calcium carbonates, optionally coated with fatty acids, especially stearates, barites, quartz flours, quartz sands, dolomites, wollastonites, kaolins, calcined kaolins, sheet silicates, such as mica or talc, zeolites, aluminum hydroxides, magnesium hydroxides, silicas, including finely divided silicas from pyrolysis processes, cements, gypsums, fly ashes, industrially produced carbon blacks, graphite, metal powders, for example of aluminum, copper, iron, silver or steel, PVC powders or hollow beads.

Suitable plasticizers are especially carboxylic acid esters, such as phthalates, especially diisononyl phthalate (DINP), diisodecyl phthalate (DIDP) or di(2-propylheptyl) phthalate (DPHP), hydrogenated phthalates, especially hydrogenated diisononyl phthalate or diisononyl cyclohexane-1,2-dicarboxylate (DINCH), terephthalates, especially dioctyl terephthalate, trimellitates, adipates, especially dioctyl adipate, azelates, sebacates, benzoates, glycol ethers, glycol esters, organic phosphoric or sulfonic acid esters, polybutenes, polyisobutenes or plasticizers derived from natural fats or oils, especially epoxidized soybean or linseed oil.

Suitable solvents are especially acetone, methyl ethyl ketone, methyl n-propyl ketone, diisobutyl ketone, methyl isobutyl ketone, methyl n-amyl ketone, methyl isoamyl ketone, acetylacetone, mesityl oxide, cyclohexanone, methylcyclohexanone, ethyl acetate, propyl acetate, butyl acetate, n-butyl propionate, diethyl malonate, 1-methoxy-2-propyl acetate, ethyl 3-ethoxypropionate, diisopropyl ether, diethyl ether, dibutyl ether, diethylene glycol diethyl ether, ethylene glycol diethyl ether, ethylene glycol monopropyl ether, ethylene glycol mono(2-ethylhexyl) ether, toluene, xylene, heptane, octane, naphtha, white spirit, petroleum ether or petroleum spirit, especially Solvesso™ products (from Exxon), and furthermore methylene chloride, propylene carbonate, butyrolactone, N-methylpyrrolidone or N-ethylpyrrolidone.

The composition may comprise further additives commonly used for polyurethane compositions. More particularly, the following auxiliaries and additives may be present:

inorganic or organic pigments, especially titanium dioxide, chromium oxides or iron oxides;

fibers, especially glass fibers, carbon fibers, metal fibers, ceramic fibers, polymer fibers, such as polyamide fibers or polyethylene fibers, or natural fibers, such as wool, cellulose, hemp or sisal;

dyes;

desiccants, especially molecular sieve powder, calcium oxide, highly reactive isocyanates, such as p-tosyl isocyanate, monomeric diisocyanates or orthformic acid esters;

adhesion promoters, especially organoalkoxysilanes, especially epoxysilanes, such as especially 3-glycidoxypropyltrimethoxysilane or 3-glycidoxypropyltriethoxysilane, (meth)acrylosilanes, anhydridosilanes, carbamatosilanes, alkylsilanes or iminosilanes, or oligomeric forms of these silanes, or titanates;

further latent hardeners or crosslinking agents, especially aldimines, ketimines, enamines or oxazolidines;

further catalysts which accelerate the reaction of the isocyanate groups, especially salts, soaps or complexes of tin, zinc, bismuth, iron, aluminum, molybdenum, dioxomolybdenum, titanium, zirconium or potassium, especially tin(II) 2-ethylhexanoate, tin(II) neodecanoate, zinc(II) acetate, zinc(II) 2-ethylhexanoate, zinc(II) laurate, zinc(II) acetylacetonate, aluminum lactate, aluminum oleate, diisopropoxytitanium bis(ethyl acetoacetate) or potassium acetate; compounds containing tertiary amino groups, especially N-ethyldiisopropylamine, N,N,N',N'-tetramethylalkylenediamines, pentamethylalkylenetriamines and higher homologs thereof, bis(N,N-diethylam inoethyl) adipate, tris(3-dimethylaminopropyl)amine, 1,4-diazabicyclo[2.2.2]octane (DABCO), 1,8-diazabicyclo

[5.4.0]undec-7-ene (DBU), 1,5-diazabicyclo[4.3.0]non-5-ene (DBN), N-alkylmorpholines, N,N'-dimethylpiperazine; aromatic nitrogen compounds, such as 4-dimethylaminopyridine, N-methylimidazole, N-vinylimidazole or 1,2-dimethylimidazole; organic ammonium compounds, such as benzyltrimethylammonium hydroxide or alkoxylated tertiary amines; what are called "delayed action" catalysts, which are modifications of known metal or amine catalysts;

rheology modifiers, especially thickeners, especially sheet silicates, such as bentonites, derivatives of castor oil, hydrogenated castor oil, polyamides, polyamide waxes, polyurethanes, urea compounds, fumed silicas, cellulose ethers or hydrophobically modified polyoxyethylenes;

natural resins, fats or oils, such as rosin, shellac, linseed oil, castor oil or soybean oil;

nonreactive polymers, especially homo- or copolymers of unsaturated monomers, especially from the group comprising ethylene, propylene, butylene, isobutylene, isoprene, vinyl acetate or alkyl (meth)acrylates, especially polyethylenes (PE), polypropylenes (PP), polyisobutylenes, ethylene/vinyl acetate copolymers (EVA) or atactic poly-α-olefins (APAO);

flame-retardant substances, especially the aluminum hydroxide or magnesium hydroxide fillers already mentioned, and also especially organic phosphoric acid esters, such as especially triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris (2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenyl phosphate), bisphenol A bis (diphenyl phosphate) or ammonium polyphosphates;

additives, especially wetting agents, leveling agents, defoamers, deaerators, stabilizers against oxidation, heat, light or UV radiation, or biocides;

or further substances customarily used in moisture-curing compositions.

It may be advisable to chemically or physically dry certain substances before mixing them into the composition.

Especially suitable as further latent hardeners are polyaldimines derived from 2,2-dimethyl-3-lauroyloxypropanal.

In the composition, the ratio of aldimino groups to isocyanate groups is preferably in the range from 0.05 to 1.1, particularly preferably 0.1 to 1.0, especially 0.2 to 0.9.

The composition preferably contains a content of polyisocyanates and of polyurethane polymers containing isocyanate groups in the range from 5% to 90% by weight, especially 10% to 80% by weight.

The composition is especially produced with exclusion of moisture and stored at ambient temperature in moisture-tight containers. A suitable moisture-tight container especially consists of an optionally coated metal and/or plastic, and is especially a drum, a transport box, a hobbock, a bucket, a canister, a can, a bag, a tubular bag, a cartridge or a tube.

The composition may be in the form of a one-component composition or in the form of a multi-component, especially two-component, composition.

A composition referred to as a "one-component" composition is one in which all constituents of the composition are in the same container and which is storage-stable per se.

A composition referred to as a "two-component" composition is one in which the constituents of the composition are in two different components which are stored in separate containers and are not mixed with one another until shortly before or during the application of the composition.

The composition is preferably a one-component composition. Given suitable packaging and storage, it is storage-stable, typically over several months, up to one year or longer.

On application of the composition, the process of curing commences. This results in the cured composition.

In the case of a one-component composition, it is applied as such and then begins to cure under the influence of moisture or water. For acceleration of the curing, an accelerator component which contains or releases water and/or a catalyst can be mixed into the composition on application, or the composition, after application thereof, can be contacted with such an accelerator component.

In the case of a two-component composition, it is applied after the mixing of the two components and begins to cure by internal reaction, and the curing may be completed by the action of external moisture. The two components can be mixed continuously or batchwise with dynamic mixers or static mixers.

In the curing, the isocyanate groups react under the influence of moisture with the aldimino groups of the polyaldimine of the formula (IV) and any further blocked amino groups present. Some of the isocyanate groups, especially the excess isocyanate groups relative to the aldimino groups, react with one another under the influence of moisture and/or with any further reactive groups present in the composition, especially hydroxyl groups or free amino groups. The totality of these reactions of isocyanate groups that lead to the curing of the composition is also referred to as crosslinking.

The moisture required for the curing of the one-component composition preferably gets into the composition through diffusion from the air (atmospheric moisture). In the process, a solid layer of cured composition is formed on the surfaces of the composition which come into contact with air ("skin"). The curing continues in the direction of diffusion from the outside inward, the skin becoming increasingly thick and ultimately encompassing the entire composition applied. The moisture can also get into the composition additionally or entirely from one or more substrate(s) to which the composition has been applied and/or can come from an accelerator component which is mixed into the composition on application or is contacted therewith after application, for example by painting or spraying.

Any external moisture required to complete the curing of a two-component composition preferably comes from the air and/or from the substrates.

The composition is preferably applied at ambient temperature, especially in the range from about 0 to 50° C., preferably in the range from 5 to 40° C.

If the composition is a hot-melt adhesive, it is preferably applied in the molten state at a temperature in the range from 80 to 180° C.

The composition is preferably cured at ambient temperature.

The composition has a comparatively long open time.

The "open time" refers to the period of time over which the composition can be worked or reworked after the curing process has commenced.

The time until formation of a skin ("skin time") or until freedom from tack ("tack-free time") is a measure of the open time.

In the crosslinking, the blocking agent, i.e. the aldehyde mixture described, is released. It is substantially nonvolatile and odorless and remains for the most part in the cured composition. It behaves or acts like a plasticizer. As such, it can in principle itself migrate and/or affect the migration of plasticizers. The blocking agent has very good compatibility with the cured composition, barely migrates itself, and also does not trigger any enhanced migration of further plasticizers.

The composition is preferably an adhesive or a sealant or a coating.

The adhesive or sealant or coating is preferably elastic.

The composition is especially suitable as an adhesive and/or sealant for bonding and sealing applications, especially in the construction and manufacturing industries or in motor vehicle construction, especially for parquet bonding, installable component bonding, cavity sealing, assembly, module bonding, vehicle body bonding, window pane bonding or joint sealing.

Elastic bondings in motor vehicle construction are, for example, the bonded attachment of parts, such as plastic covers, trim strips, flanges, fenders, driver's cabins or other installable components, to the painted body of a motor vehicle, or the bonding of glass panes into the vehicle body, where the motor vehicles are especially automobiles, trucks, buses, rail vehicles or ships.

The composition is especially suitable as sealant for the elastic sealing of all kinds of joints, seams or cavities, especially of joints in construction, such as expansion joints or connection joints between structural components. A sealant having flexible properties is particularly suitable especially for the sealing of expansion joints in built structures.

As coating, the composition is suitable for the protection of floors or walls, especially as coating of balconies, terraces, open spaces, bridges, parking levels, or for the sealing of roofs, especially flat roofs or slightly inclined roof areas or roof gardens, or in the interior of buildings for water sealing, for example beneath tiles or flagstones in plumbing units or kitchens, or as floor covering in kitchens, industrial buildings or manufacturing spaces, or as seal in collection tanks, channels, shafts or wastewater treatment plants, or for the protection of surfaces as varnish or seal, or as casting compound for cavity sealing, as seam seal or as protective coating for pipes, for example.

It can also be used for repair purposes as seal or coating, for example of leaking roof membranes or floor coverings no longer fit for purpose, or especially as repair compound for highly reactive spray seals.

The composition can be formulated such that it has a pasty consistency with structurally viscous properties. A composition of this kind is applied by means of a suitable device, for example from commercial cartridges or kegs or hobbocks, for example in the form of a bead, which may have an essentially round or triangular cross-sectional area.

The composition can furthermore be formulated such that it is fluid and "self-leveling" or only slightly thixotropic and can be poured out for application. As coating, it can, for example, subsequently be distributed flat up to the desired layer thickness, for example by means of a roller, a slide bar, a toothed applicator or a trowel. In one operation, typically a layer thickness in the range from 0.5 to 3 mm, especially 1.0 to 2.5 mm, is applied.

Suitable substrates which can be bonded or sealed or coated with the composition are especially

- glass, glass ceramic, concrete, mortar, fiber cement, especially fiber cement boards, brick, tile, gypsum, especially gypsum boards, or natural stone, such as granite or marble;
- repair or leveling compounds based on PCC (polymer-modified cement mortar) or ECC (epoxy resin-modified cement mortar);
- metals or alloys, such as aluminum, copper, iron, steel, nonferrous metals, including surface-finished metals or alloys, such as zinc-plated or chromium-plated metals;
- asphalt or bitumen;
- leather, textiles, paper, wood, wood materials bonded with resins, such as phenolic, melamine or epoxy resins, resin/textile composites or further materials called polymer composites;
- plastics, such as rigid and flexible PVC, polycarbonate, polystyrene, polyester, polyamide, PMMA, ABS, SAN, epoxy resins, phenolic resins, PUR, POM, TPO, PE, PP, EPM or EPDM, in each case untreated or surface-treated, for example by means of plasma, corona or flames;
- fiber-reinforced plastics, such as carbon fiber-reinforced plastics (CFP), glass fiber-reinforced plastics (GFP) and sheet molding compounds (SMC);
- insulation foams, especially made of EPS, XPS, PUR, PIR, rock wool, glass wool or foamed glass;
- coated or painted substrates, especially painted tiles, coated concrete, powder-coated metals or alloys or painted metal sheets;
- paints or varnishes, especially automotive topcoats.

If required, the substrates can be pretreated prior to application, especially by physical and/or chemical cleaning methods or the application of an activator or a primer.

It is possible to bond and/or seal two identical or two different substrates.

The application and curing of the composition affords an article bonded or sealed or coated with the composition. This article may be a built structure or a part thereof, especially a built structure in civil engineering above or below ground, a bridge, a roof, a staircase or a facade, or it may be an industrial good or a consumer good, especially a window, a pipe, a rotor blade of a wind turbine, a domestic appliance or a mode of transport, such as especially an automobile, a bus, a truck, a rail vehicle, a ship, an aircraft or a helicopter, or an installable component thereof.

The composition according to the invention has advantageous properties. It is storage-stable with exclusion of moisture, even together with the highly reactive aromatic isocyanate groups. It has a sufficiently long open time to make possible a seamless distribution of the material applied or a positioning or readjustment of the objects bonded therewith over a certain period after application, which is important, for example, in the case of coatings over a large area or long sealing strips, or in the case of bonding of large or complex objects. The curing takes place in a fast, reliable and blister-free fashion without disruptive immissions of odor, so that the composition can be used without limitation even under climatically unfavorable conditions, such as high air humidity and/or high temperature or with use of aqueous accelerator components, and also can be used unhesitatingly even in interior spaces or in large-area applications. On curing, it rapidly builds up strength, the skin formed on the surface being really soon surprisingly nontacky and dry, which is very valuable especially in application on building sites, since contamination by, for example, dust is thereby prevented. The curing takes place completely and results in a high-quality material which combines a high mechanical strength and extensibility with a moderate modulus of elasticity and consequently is also suitable for flexible products. Despite its content of liberated nonvolatile blocking agent, the composition shows scarcely any defects produced by plasticizer migration, such as bleeding, discoloration, formation of specks, softening or substrate detachment, and can consequently be used, without limitation, even on porous substrates or on plastics which form stress cracks and in combination with outer layers.

EXAMPLES

Exemplary embodiments are cited below, which are intended to further illustrate the invention described. Of course, the invention is not limited to these exemplary embodiments described.

"Standard climatic conditions" refer to a temperature of 23±1° C. and a relative air humidity of 50±5%.

Description of the Measurement Methods:

The amine value (including blocked amino groups) was determined by means of titration (with 0.1N $HClO_4$ in acetic acid versus crystal violet).

The viscosity was measured with a thermostated Rheotec RC30 cone-plate viscometer (cone diameter 50 mm, cone angle 1°, cone tip-plate distance 0.05 mm, shear rate 10 $s^{-1}$).

The crystallization temperature or glass transition temperature was determined by means of DSC with a Mettler Toledo DSC 3+ 700 device in a temperature range from −80 to +50° C. with a heating rate of 5 K/m in.

Aldehydes Used:

Aldehyde-1: Crude product from formylation, catalyzed by means of $HF-BF_3$, of $C_{10-14}$-alkylbenzene with carbon monoxide after distillative separation of the low-molecular-weight constituents, containing 85%-90% by weight of predominantly branched 4-($C_{10-14}$-alkyl)benzaldehydes and 10%-15% by weight of high-boiling-point or high-molecular-weight alkylbenzene compounds (measured by GC-FID); average aldehyde equivalent weight 309 g/eq; Gardner color standard number 10.

Aldehyde-2: Fractionated aldehyde mixture from the overhead distillation of aldehyde-1 under high vacuum, containing >98% by weight of predominantly branched 4-($C_{10-14}$-alkyl)benzaldehydes (measured by GC-FID); average aldehyde equivalent weight 290 g/eq; Gardner color standard number 3.

Aldehyde-3: 2,2-Dimethyl-3-lauroyloxypropanal (284.4 g/mol)

Aldehyde-1 is an aldehyde mixture according to the invention. The corresponding distillatively purified aldehyde-2, from which the high-boiling-point byproducts have been separated, and also the aldehyde-3 are used as comparison.

Preparation of Blocked Amines or Latent Hardeners:

Aldimine A-1:

106.06 g of aldehyde-1 were introduced into a round-bottomed flask under a nitrogen atmosphere. 27.86 g of 3-aminomethyl-3,5,5-trimethylcyclohexylamine (Vestamin® IPD, from Evonik) were added with stirring and the volatile constituents were subsequently removed at 80° C. and under a vacuum of 10 mbar. A light-colored odorless liquid having a viscosity of 10.7 Pa·s at 20° C., an amine value of 143.5 mg KOH/g and a crystallization temperature of −46.1° C. was obtained.

Aldimine A-2:

106.06 g of aldehyde-1 were introduced into a round-bottomed flask under a nitrogen atmosphere. 27.20 g of a 70% aqueous solution of 1,6-hexanediamine (from Sigma-Aldrich) were added with stirring and the volatile constituents were subsequently removed at 80° C. and under a vacuum of 10 mbar. A light-colored odorless liquid having a viscosity of 0.7 Pa·s at 20° C., an amine value of 158.6 mg KOH/g and a crystallization temperature of −66.5° C. was obtained.

Aldimine R-1:

100.00 g of aldehyde-2 were introduced into a round-bottomed flask under a nitrogen atmosphere. 27.86 g of 3-aminomethyl-3,5,5-trimethylcyclohexylamine (Vestamin® IPD, from Evonik) were added with stirring and the volatile constituents were subsequently removed at 80° C. and under a vacuum of 10 mbar. A pale-yellow odorless liquid having a viscosity of 25.3 Pas at 20° C., an amine value of 152.1 mg KOH/g and a crystallization temperature of −40.6° C. was obtained.

Aldimine R-2:

100.00 g of aldehyde-2 were introduced into a round-bottomed flask under a nitrogen atmosphere. 27.20 g of a 70% aqueous solution of 1,6-hexanediamine (from Sigma-Aldrich) were added with stirring and the volatile constituents were subsequently removed at 80° C. and under a vacuum of 10 mbar. A pale-yellow odorless liquid having a viscosity of 1.0 Pas at 20° C., an amine value of 169.4 mg KOH/g and a crystallization temperature of −63.8° C. was obtained.

Aldimine R-3:

50.00 g of aldehyde-3 were introduced into a round-bottomed flask under a nitrogen atmosphere. 13.93 g of 3-aminomethyl-3,5,5-trimethylcyclohexylamine (Vestamin® IPD, from Evonik) were added with stirring and the volatile constituents were subsequently removed at 80° C. and under a vacuum of 10 mbar. A pale-yellow odorless liquid having a viscosity of 0.2 Pas at 20° C. and an amine value of 153.0 mg KOH/g was obtained.

The aldimines A-1 and A-2 are latent hardeners according to the invention and correspond to the formula (IV).

The aldimines R-1 and R-2 and R-3 are used as comparison.

Preparation of Polymers Containing Isocyanate Groups

Polymer P1:

400 g of polyoxypropylene diol (Acclaim® 4200, from Covestro; OH number 28.5 mg KOH/g) and 52 g of diphenylmethane 4,4'-diisocyanate (Desmodur® 44 MC L, from Covestro) were reacted by a known process at 80° C. to give an NCO-terminated polyurethane polymer which is liquid at room temperature and has a content of free isocyanate groups of 1.85% by weight.

Polymer P2:

590 g of polyoxypropylene diol (Acclaim® 4200, from Covestro; OH number 28.5 mg KOH/g), 1180 g of polyoxypropylene/polyoxyethylene triol (Caradol® MD34-02, from Shell; OH number 35.0 mg KOH/g) and 230 g of isophorone diisocyanate (Vestanat® IPDI, from Evonik) were reacted by a known process at 80° C. to give an NCO-terminated polyurethane polymer which is liquid at room temperature and has a content of free isocyanate groups of 2.10% by weight.

Polymer P3:

300.0 g of polyoxypropylene/polyoxyethylene diol (Desmophen® L300, from Covestro; OH number 190.0 mg KOH/g) and 228.8 g of isophorone diisocyanate (Vestanat® IPDI, from Evonik) were reacted by a known process at 60° C. to give an NCO-terminated polyurethane polymer which is liquid at room temperature and has a content of free isocyanate groups of 7.91% by weight.

Polyurethane Compositions (One-Component)

Compositions Z1 to Z6

For each composition, the ingredients specified in table 1 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture. Each composition was tested as follows:

As a measure of storage stability, the Viscosity (1d RT) was determined the day after production, and the Viscosity (7d 60° C.) was determined after storage for 7 days in a closed container in a 60° C. warm air circulation oven, as described above.

As a measure of the open time, the Tack-free time was determined. For this purpose, a few grams of the composition were applied to cardboard in a layer thickness of about 2 mm and, under standard climatic conditions, the time until, when the surface of the composition was gently tapped by means of an LDPE pipette, there were for the first time no residues remaining any longer on the pipette was determined.

To determine the mechanical properties, each composition was poured onto a PTFE-coated film to give a film of thickness 2 mm and stored under standard climatic conditions for 7 days, and a few dumbbells having a length of 75 mm with a bar length of 30 mm and a bar width of 4 mm were punched out of the film and these were tested in accordance with DIN EN 53504 at a pull rate of 200 mm/minute for Tensile strength (breaking force), Elongation at break, Modulus of elasticity 5% (at 0.5%-5% elongation) and Modulus of elasticity 50% (at 0.5%-50% elongation).

The Appearance was assessed visually on the films produced. "Nice" was used to describe a clear film with a nontacky surface without blisters.

The Odor was assessed by smelling by nose at a distance of 2 cm from the freshly produced films. "Yes" means that an odor was clearly perceptible. "No" means that no odor was perceptible.

The results are reported in table 1.

The compositions labeled with (Ref) are comparative examples.

TABLE 1

Composition (in parts by weight) and properties of Z1 to Z6.

| Composition | Z1 | Z2 (Ref) | Z3 | Z4 (Ref) | Z5 | Z6 (Ref) |
|---|---|---|---|---|---|---|
| Polymer P1 | 80.00 | 80.00 | 80.00 | 80.00 | — | — |
| Polymer P2 | — | — | — | — | 80.00 | 80.00 |
| Aldimine | A-1 | R-1 | A-2 | R-2 | A-1 | R-1 |
| | 9.63 | 9.09 | 8.71 | 8.16 | 10.94 | 10.32 |
| Salicylic acid solution[1] | 1.50 | 1.50 | 1.50 | 1.50 | 1.50 | 1.50 |
| Viscosity (1 d RT) | 29 | 31 | 43 | 51 | 13 | 14 |
| [Pa · s] (7 d 60° C.) | 31 | 33 | 60 | 80 | 14 | 15 |
| Tack-free time | 115' | 105' | 47' | 50' | 195' | 180' |
| Tensile strength [MPa] | 1.50 | 1.44 | 3.25 | 2.40 | 1.27 | 1.23 |
| Elongation at break [%] | 1778 | 1809 | 609 | 357 | 237 | 213 |
| Modulus of elasticity 5% [MPa] | 0.72 | 0.77 | 6.75 | 6.59 | 1.19 | 1.25 |
| Modulus of elasticity 50% | 0.25 | 0.39 | 1.81 | 1.82 | 0.72 | 0.79 |
| Appearance | nice | nice | nice | nice | nice | nice |
| Odor | no | no | no | no | no | no |

[1]5% in dioctyl adipate

Compositions Z7 to Z10

For each composition, the ingredients specified in table 2 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture. Each composition was tested as follows:

As a measure of plasticizer migration, speck formation on cardboard was determined. For this purpose, each composition was applied to a piece of cardboard such that it had a round base area of diameter 15 mm and a height of 4 mm, and was stored under standard climatic conditions for 7 days. Around each composition, thereafter, a dark oval speck had formed on the cardboard. The dimensions thereof (height and width) were measured and reported in table 2 as Migration.

TABLE 2

Composition (in parts by weight) and properties of Z7 to Z10.

| Composition | | Z7 | Z8 (Ref) | Z9 (Ref) | Z10 (Ref) |
|---|---|---|---|---|---|
| Polymer P3 | | 15.00 | 15.00 | 15.00 | 15.00 |
| Chalk | | 15.00 | 15.00 | 15.00 | 15.00 |
| Silica | | 1.13 | 1.13 | 1.13 | 1.13 |
| Aldimine | | A-1 | R-1 | R-3 | — |
| | | 5.82 | 5.49 | 5.46 | |
| Salicylic acid solution[1] | | 3.00 | 3.00 | 3.00 | 3.00 |
| DBTDL solution[2] | | 1.50 | 1.50 | 1.50 | 1.50 |
| Migration | Height | 22 | 21 | 33 | 19 |
| (7 d) [mm] | Width | 25 | 23 | 28 | 19 |
| Odor | | no | no | no | no |

[1]5% in dioctyl adipate

[2]5% dibutyltin dilaurate in diisodecyl phthalate

The invention claimed is:

1. A method comprising:

reacting an aldehyde mixture comprising:

70% to 92% by weight of aldehydes of the formula (I), in which R is an alkyl group having 6 to 20 carbon atoms, and

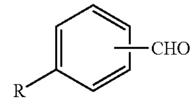

(I)

8% to 30% by weight of alkylbenzene compounds not corresponding to the formula (I), with an amine to be blocked such that the amine is in a chemically blocked form.

2. The method of claim 1, wherein the alkylbenzene compounds not corresponding to the formula (I) have a higher boiling point than the aldehydes of the formula (I).

3. The method of claim 1, wherein a majority of the alkyl groups R of the aldehydes of the formula (I) in the aldehyde mixture have a structure that is branched.

4. The method of claim 1, wherein the formyl group of the formula (I) is in the para position relative to the R group.

5. The method of claim 1, wherein the aldehydes of the formula (I) are selected from 4-decylbenzaldehydes,
4-undecylbenzaldehydes,
4-dodecylbenzaldehydes,
4-tridecylbenzaldehydes and
4-tetradecylbenzaldehydes, where the alkyl groups of which are branched.

6. The method of claim 1, wherein the alkylbenzene compounds not corresponding to the formula (I) comprise one or more compounds of the formulae

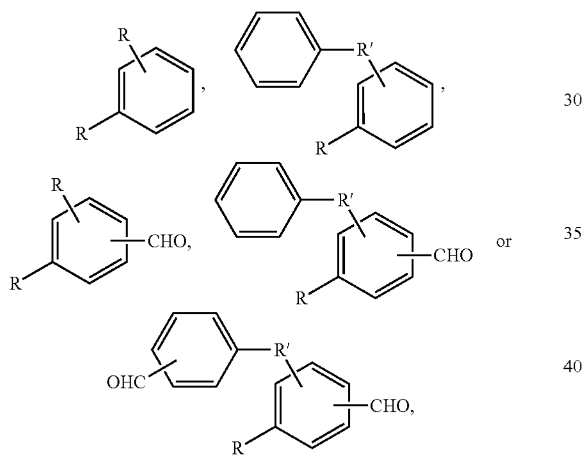

in which R' is an alkylene group having 6 to 20 carbon atoms.

7. The method of claim 1, wherein the aldehyde mixture is a reaction product of a formylation of at least one alkylbenzene of the formula

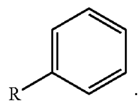

8. The method of claim 7, wherein the formylation was carried out with carbon monoxide in the presence of hydrofluoric acid and boron trifluoride.

9. The method of claim 1, wherein the amine to be blocked has at least one primary or secondary amino group and additionally at least one reactive group selected from primary amino group, secondary amino group, hydroxyl group and silane group.

10. The method of claim 1, wherein the amine to be blocked is selected from the group consisting of primary aliphatic diamines,
primary aromatic diamines,
primary aliphatic triamines,
aliphatic diamines having a primary and a secondary amino group,
aliphatic polyamines having two primary and a secondary amino group,
aminoalcohols,
dialkanolamines,
aminosilanes and
alkanolaminosilanes.

11. The method of claim 1, wherein the aldehyde mixture is reacted with the amine to be blocked so that the aldehyde mixture is combined with the amine to give a reaction mixture, optionally with addition of a solvent, the aldehyde groups being present, with regard to the primary and secondary amino groups, stoichiometricaly or in stoichiometric excess, and the condensation water produced in the reaction and optionally solvent used during or after the combining are removed from the reaction mixture using a suitable method, optionally with heating of it and/or application of vacuum.

12. A blocked amine obtained from reacting an aldehyde mixture comprising:

70% to 92% by weight of aldehydes of the formula (I), in which R is an alkyl group having 6 to 20 carbon atoms, and

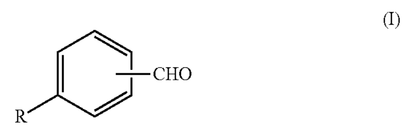

8% to 30% by weight of alkylbenzene compounds not corresponding to the formula (I), with an amine to be blocked such that the amine is in a chemically blocked form.

13. The blocked amine as claimed in claim 12, wherein the blocked amine has functional groups of the formulae (II) and/or (III),

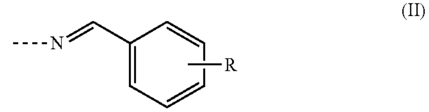

in which

X is O or S or $NR^0$, in which $R^0$ is a monovalent organic group having 1 to 18 carbon atoms, Y is a 1,2-ethylene or 1,3-propylene group.

14. A composition containing isocyanate groups comprising at least one blocked amine as claimed in claim 12.

15. The composition containing isocyanate groups as claimed in claim 14, the composition comprising:

at least one polyisocyanate and/or at least one polyurethane polymer containing isocyanate groups, and at least one polyaldimine of the formula (IV), in which

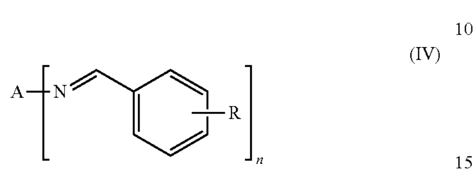

(IV)

n is 2 or 3, and

A is an non-polymeric n-valent organic radical having a molecular weight in the range from 28 to 10,000 g/mol, or A is a polymeric n-valent organic radical where a number-average molecular weight Mn of the polymeric A groups of the at least one polyaldimine of the formula (IV) in the composition is less than 10,000 g/mol, the number-average molecular weight Mn being determined by means of gel permeation chromatography (GPC) against polystyrene as a standard.

* * * * *